United States Patent [19]

Mostyn, Jr.

[11] 4,257,709
[45] Mar. 24, 1981

[54] AUTOMATIC BLANKING CIRCUIT

[75] Inventor: William T. Mostyn, Jr., Waco, Tex.

[73] Assignee: Helena Laboratories Corporation, Beaumont, Tex.

[21] Appl. No.: 106,437

[22] Filed: Dec. 26, 1979

[51] Int. Cl.³ ............................................. G01N 21/00
[52] U.S. Cl. ..................................... 356/435; 250/565; 356/40
[58] Field of Search ................. 356/40, 434, 435, 425; 250/564, 565, 575, 345

[56] References Cited

U.S. PATENT DOCUMENTS

| | | | |
|---|---|---|---|
| 3,528,749 | 9/1970 | Bowker | 356/435 |
| 3,678,505 | 7/1972 | Mostyn | 324/99 D |
| 3,992,113 | 11/1979 | Egli et al. | 356/435 |

Primary Examiner—R. A. Rosenberger
Attorney, Agent, or Firm—Cullen, Sloman, Cantor, Grauer, Scott & Rutherford

[57] ABSTRACT

In an optical system including a light source and a photodetector, a circuit and method for compensating for degradation of the optical system which may include deterioration in the intensity of the light source, caused by a variety of factors such as dirt, aging of the light source, etc., or dirt on the photodetector. The intensity of the light from the light source as received by the photodetector is repeatedly measured and an average value determined which accurately indicates the intensity of the light received. Subsequent use of the optical system includes comparison to the most recent average value of light received by the photodetector. Hence the present system eliminates the need for repeated calibration of the optical system by providing the same effect as though the system were being repeatedly and automatically calibrated to account for system degradation.

12 Claims, 1 Drawing Figure

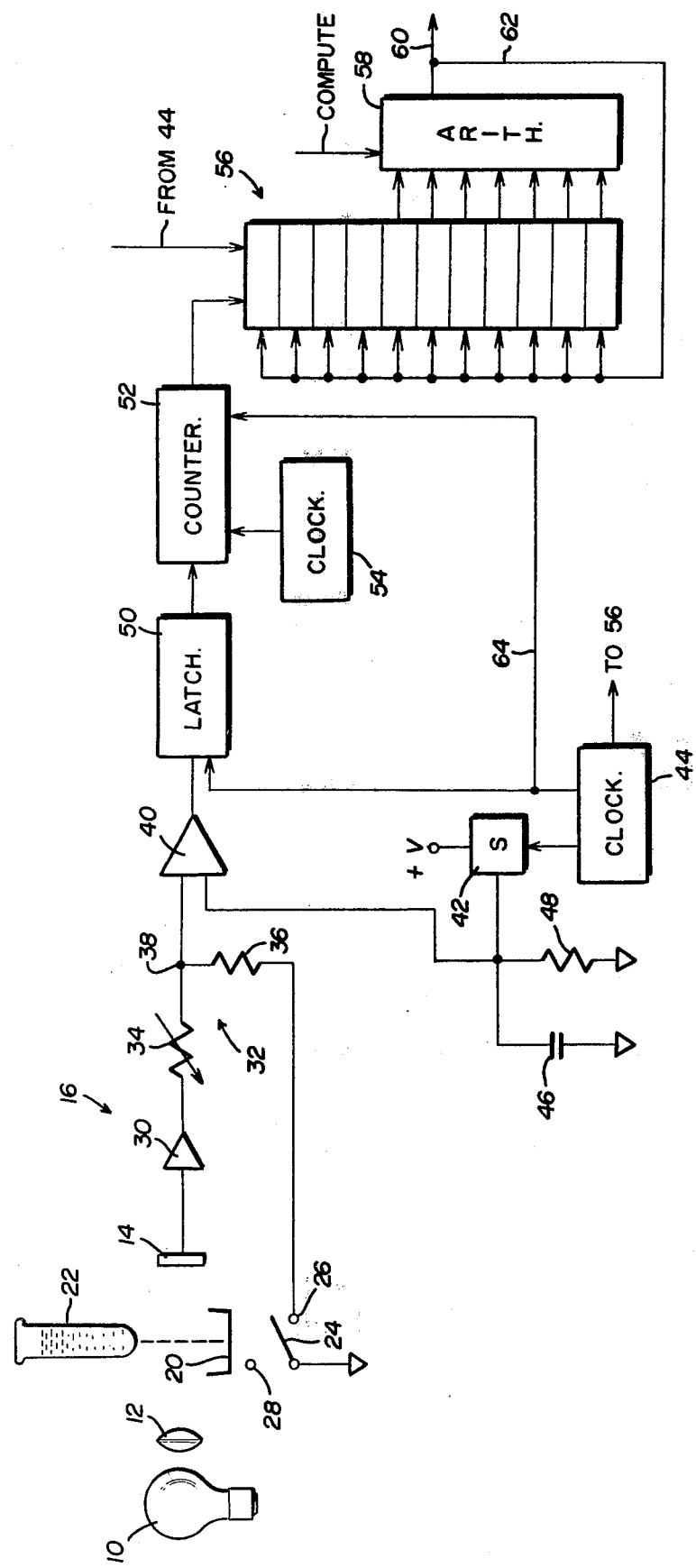

AUTOMATIC BLANKING CIRCUIT

CROSS-REFERENCE TO RELATED APPLICATIONS

The Automatic Blanking Circuit of the present invention may be utilized in an optical system such as that described in the co-pending application owned by the Assignee of the present invention entitled Method and Apparatus for Automated Determination of Hemoglobin Species, Ser. No. 106,438, filed Dec. 26, 1979.

BACKGROUND OF THE INVENTION

The present invention relates generally to optical systems including a light source and a photodetector where the photodetector provides an output signal having an intensity proportional to the amount of light received by the photodetector. More particularly, the present invention relates to an automatic blanking circuit for such an optical system to automatically compensate for variations in intensity of the light source caused by age, deterioration or even dirt on the light source or the photodetector. The present invention may be utilized in connection with any one of a number of optical systems including but not limited to systems employed in clinical laboratory equipment where absorbance of light by a sample, or transmittance of light through a sample, or reflectivity of light from a sample is detected by the photodetector. Outside the clinical laboratory field, the present invention may be utilized in optical systems where absorbance, reflectivity, or opaqueness is being measured such as, for example, optical readers and optical character recognition systems.

Since one use of the present invention is as a part of a spectrophotometer in connection with measuring the concentration of a substance in solution and, more specifically, for determining hemoglobin species in a blood sample, the invention will be explained in that context. Such explanation, however, should not be construed as limiting the applicability of the automatic blanking circuit.

By way of further background, when measuring the concentration of a substance such as hemoglobin in solution, the concentration of the substance measured photometrically usually follows Beer's Law where the negative logarithm of the transmittance varies as a function of the concentration. Specifically the formula is log $(I/I_o) = -KC$, where the ratio $(I/I_o)$ is referred to as the transmittance of light, i.e., the light which is not absorbed by the sample. In the formula, the transmittance, $I/I_o$ is the ratio of the intensity of a beam of light passing through the solution divided by the intensity of the same beam of light passing through a "blank" solution, i.e., a solution containing a zero concentration of the substance to be measured. Thus it is important that the "same" beam of light be used for both measurements, i.e., there must be no aging or degradation of the optical system between measurements.

In order to achieve the desired results, it is initially necessary to determine the transmittance of a zero concentration solution. According to the prior art, this is usually done by inserting a vial containing a blank or zero concentration solution, often water, into the path of light between the light source and a photodetector, and adjusting the output to 100% transmittance. This adjustment may be accomplished in several ways according to the prior art. First, the intensity of the light source itself may be varied. Second, the intensity of the amount of light in the light path to the solution may be varied by a diaphragm or variable slit. Third, a 100% transmittance value can be achieved by varying the sensitivity of the photodetector. Finally, since the ultimate output is usually determined by an indicator such as a meter, the 100% transmittance value can be achieved by varying the internal resistance of the meter, through a conventional potentiometer, so that the meter reading is 100% transmittance when a blank vial is inserted in the path between the light source and the photodetector.

There are many disadvantages in each of the above techniques in that they all require manual adjustments by the operator of the equipment. In addition, the basic shortcoming of each of these techniques is that each fails to account for aging or variations in the intensity of the light source or dirt in the optical system. While a potential solution to this problem has been suggested in U.S. Pat. No. 4,128,339, such solution still requires a multiple step manual calibration followed by a computer operation in an attempt to provide an accurate transmittance value. In the system of the aforementioned patent, if the calibration occurs once each day, any aging of the light source or dirt in the optical system between calibrations will still not be accounted for and erroneous readings will result.

The present invention overcomes these problems by providing a blanking circuit which automatically compensates for any degradation in the optical system.

SUMMARY OF THE INVENTION

The present invention provides an automatic blanking circuit which may be used with a spectrophotometer or other optical detection system which system provides an output signal relative to the amount of light reaching a photodetector and furthermore which repeatedly and continuously self-adjusts for degradation of the optical system between successive evaluations of samples by the system. Thus the present system continually self-calibrates to compensate for degradation of the optical system.

For example, in a clinical laboratory where the operator of a spectrophotometer including the present invention will be measuring the concentration of hemoglobin in a series of blood samples, (i.e., a series of values of "I" in the formula) the present system automatically blanks or self-calibrates (i.e., adjusts the value of $I_o$) between the testing of each sample so that in all instances any degradation of the optical system is automatically accounted for. In this way any aging will be accounted for substantially when it occurs rather than only when the operator chooses to manually calibrate a system as in the prior art.

According to the present invention, the automatic blanking occurs whenever there is no vial in the spectrophotometer and the intensity of the light source reaching the photodetector ($I_o$) is determined approximately twice per second. The eleven most recent determinations of light intensity are stored and when the lid of the instrument is opened so that a vial containing a sample may be inserted into the instrument, the instrument automatically calculates the average intensity of the seven oldest readings in storage to accurately determine the most recent reliable value of $I_o$ for the system. In actual use in a spectrophotometer, as described in the aforementioned co-pending application, the value log ($I/I_o$) is actually determined as $\log I - \log I_o$. Hence the automatic blanking circuit repeatedly determines the value of $\log I_o$ when there is no vial in the instrument. The value of $\log I_o$ is stored in memory which is not part of the invention of this application. Hence for the purpose of the blanking circuit of this invention, the value of $\log I_o$ is described as the output of the circuit.

BRIEF DESCRIPTION OF THE DRAWINGS

The various objects, benefits and advantages of the present invention, together with other objects and advantages which may be attained by its use, will become more apparent upon reading the following detailed description of the invention taken in conjunction with the drawings.

In the drawings, the single FIGURE illustrates the circuit of present invention.

DETAILED DESCRIPTION OF THE INVENTION

With reference to the single FIGURE of drawings, prior to an explanation of such FIGURE, it should be recalled that the logarithm of the transmittance ($I/I_o$) varies negatively with the concentration of the solution. Thus the present system, while determining the intensity of light reaching the photodetector, uses a logarithmic conversion with respect to a reference voltage to provide the desired output. Such a logarithmic conversion is explained in greater detail in my prior U.S. Pat. No. 3,678,505.

With reference to the drawing, the present system includes a light source 10 from which the light rays are focused by a lens and filter system 12 and aimed at a photodetector 14. The output of the photodetector 14, which is a signal varying in intensity with the light received, is coupled to an amplifier means 16. In the path between the lens 12 and the photodetector 14 there is a well 20 or receptacle to receive a vial 22. The vial 22 typically contains a sample solution the concentration of which is to be determined. Positioned in the bottom of the well 20 is a switch 24 having two terminals 26 and 28. The switch 24 is a normally closed switch with the wiper connected to terminal 26 when the switch is closed. The switch is opened when the vial is inserted in the well and this causes the wiper arm of the switch to move from terminal 26 to terminal 28.

The amplifier means 16 includes an amplifier 30 which receives its input from the output of the photodetector 14. The output of the amplifier 30 is coupled through a voltage divider 32 comprising the combination of a first resistor 34 such as a potentiometer and a second resistor 36. One side of resistor 36 is connected to resistor 34 and the other side of resistor 36 is connected to the terminal 26 of the switch 24. The output from the amplifier means 16 is taken from the junction 38 of the two resistors which comprise the voltage divider. This output from junction 38 serves as one input to a dual or two-input comparator 40. The other input to the two-input comparator 40 is a logarithmically decaying voltage which is provided by a reference voltage means. Specifically, when a switch 42 is closed and then opened by pulses from a first clock 44, a voltage is supplied through the switch 42 to one side of a capacitor 46. The other side of capacitor 46 is coupled directly to system ground. A resistor 48 is connected in parallel between the switch 42 and ground across the capacitor 46 to provide a discharge path for the voltage on the capacitor 46. The second input to the comparator 40 is taken from the junction of capacitor 46 and resistor 48.

An analog to digital conversion means is provided to convert the output of the comparator 40 into a digital value representative of the time during which the light received by the photodetector 14 is less than the voltage on the discharging capacitor 46. Specifically, the output from the comparator 40 is coupled to close a latch 50. The output from the latch 50 is connected as a starting signal to a digital counter 52. A second clock 54, providing pulses at a clock rate of 7500 per 512 milliseconds provides the pulses to be counted by the counter 52. The first clock 44 provides one pulse, having a duration of 20 milliseconds, every 512 milliseconds to control the recharging of the capacitor 46, as previously described, and also to open the latch 50 on the trailing edge of each 20 millisecond pulse. The latch 50 is opened by the pulse which recharges the capacitor and closed by the output of the comparator 40. Since the first clock 44 provides a pulse every 512 milliseconds (approximately twice per second) the value of $I_o$ is thus being repeatedly counted approximately twice per second.

Each of the successive values counted by the counter 52 is serially stored in a storage memory. Specifically, the output from the counter 52 is transferred in response to a pulse from clock 44 into a memory 56 which memory serially stores eleven sequential outputs from the counter 52. Memory 56 functions as a serial shift register so that as a new output is received from the counter 52 every 512 milliseconds, the pre-existing outputs stored in memory 56 are each shifted serially down one level. Since values in the lower most level of the shift register memory 56 cannot be shifted, then when a new value is shifted into the lower most level of the memory 56 the pre-existing value in such lower most level is discarded.

According to the principles of the present invention, means are also provided to obtain an average value of the intensity of the light received by the photodetector. In a typical clinical laboratory instrument such as a spectrophotometer, the instrument has a lid or cover which is to be closed when the concentration of the sample in the vial 22 is being measured. Opening the cover permits extraneous light, other than light from the source 10, to be received by the photodetector 14. Accordingly, I have discovered that a more reliable determination of the intensity of the light source may be obtained by ignoring the most recent readings from the counter 52 which are stored in memory as these are most likely to be at least partially the result of extraneous light as the cover or lid of the instrument is being removed.

Thus, in accordance with the aforementioned principles of ignoring the most recent readings from the counter 52, my invention includes arithmetically averaging certain of the values in the memory 56. In the preferred embodiment, where eleven different values are stored in the memory, I average the seven oldest values. This is done in an arithmetic unit 58 which could be a combination of a summing circuit and a dividing circuit. The result of the arithmetic operation may be provided along an output lead 60. Simultaneously, the result of the arithmetic operation is provided and an input back to all eleven levels of the serial shift register memory 56 via lead 62.

In a preferred embodiment of the present invention, all of the clock and pulsing functions as well as counting, storage in memory, memory shifting and computation is performed in a microprocessor such as a Motorola 6800 or Motorola 6802. However, for the purpose of completeness, the above circuit description has been given.

Prior to explaining the operation of the circuit in greater detail, one additional feature should be explained. This feature, which is optional, involves a preferred factory or initial adjustment which must be performed onetime only when the circuit is being utilized in a spectrophotometer. Specifically, it should be appreciated that when a vial 22 of clear water is inserted in the well 20 there may be a slight absorption of light from the source 10. It is preferred to account for such slight absorption of light by providing an adjustment in the voltage divider 32 such that the output of the amplifier means 16 at the junction 38 is the same when no vial is in the well 20 as when a vial of water (also known as zero concentration) is in the well. To accomplish this initial adjustment, a volt meter may be connected at the junction 38 and a vial 22 of clear water inserted in the well 20. The insertion of the vial 22 in the well 20 moves the wiper arm of switch 24 to terminal 28 so that resistor 36 is not part of the voltage divider circuit. The voltage at junction 38 is determined and then the vial is removed from the well 20 thereby causing the switch 24 to revert to its normally closed position at terminal 26 thus making resistor 36 a part of the circuit. The potentiometer 34 is now adjusted to provide the same reading on the volt meter at junction 38. In this way, the voltage at junction 38 is always the same whether there is a vial of zero concentration in the well or whether there is no vial in the well.

The operation of the circuit will now be explained in the context of a spectrophotometer where a lid or cover is used to operate the device. The lid or cover being opened actuates a microswitch to initiate the operation of the arithmetic circuit 58 to compute a blank value. The first clock 44 provides a 20 millisecond pulse and the voltage through switch 42 charges the capacitor 46. Since the first clock 44 has a pulse rate of one pulse every 512 milliseconds, which is approximately one pulse every one-half second, the operation of the circuit during the next one-half second will now be explained. The charge or voltage on the capacitor 46 starts to discharge or decay through the resistor 48. During the time that the intensity of light received by the photodetector 14 and amplified by the amplifier means 16 and thereafter provided as one input to the comparator 40 is less than the decaying voltage on the capacitor 46, the latch 50 is open and the counter 52 starts counting pulses at a rate of 7500 pulses per 512 milliseconds. As soon as the charge on the capacitor drops below the voltage supplied to the comparator 40, the output of the comparator 40 goes low thus closing the latch 50 so that the counter 52 is no longer incremented. On the leading edge of the next pulse from the first clock 44, the value in the counter is shifted into memory 56 and the counter is reset by the clock pulse on lead 64. The operation is repeated during the next 512 millisecond interval with a charging of the capacitor 46 and a counting by the counter 52 at the rate of 7500 clock pulses per 512 milliseconds, the time during which the voltage on the capacitor exceeds the amplified voltage at junction 38. At the end of the next 512 millisecond interval, the output of the counter is shifted into the memory 56 and each value already in memory 56 is shifted down one level.

At the time when the lid or cover of the spectrophotometer instrument is lifted, the microswitch is closed thus providing a "compute" signal to the arithmetic unit 58. This causes the arithmetic unit 58 to average the seven oldest values in the shift register to provide an output value on lead 60 and simultaneously that average value is entered, along lead 62 back into all eleven levels of the shift register.

In summary, the automatic blanking circuit of the present invention determines the intensity of light received by a photodetector once every 512 milliseconds and stores the eleven most recent values in memory. These eleven values occurred during the preceding $11 \times 0.512$ or 5.632 seconds. Then, in response to a compute signal, the seven oldest values are averaged. In so doing, the four most recent values, which occurred during the preceding $4 \times 0.512$ or 2.048 seconds are ignored.

Thus, the present system automatically adjusts for degradation of the optical system by providing, automatically, the equivalent of a calibration.

The foregoing is a complete description of the principles of operation and the circuit for the present invention. Various modifications can be made without departing from the spirit and scope of my invention. My invention, therefore, should be limited only by the scope of the following claims.

What is claimed is:

1. An optical system where light from a source is transmitted through a sample to measure the absorbance of light by the sample, the improvement of an automatic blanking circuit to continually compensate for variations in the intensity of the light received by a photodetector, such as those caused by age, deterioration, dirt or the like, comprising:

a source of reference voltage;
comparator means for comparing the reference voltage to the output of said photodetector;
an analog to digital converter for providing a digital value representative of the time during which the reference voltage exceeds the intensity of light received by said photodetector;
storage means for serially storing a first predetermined number of outputs from said analog to digital converter; and
means for averaging a second predetermined number of values in said storage means and providing an output; said second predetermined number being less than said first predetermined number.

2. The invention as defined in claim 1 wherein said storage means also receives the output from said averaging means.

3. The invention as defined in claim 1 wherein said storage means stores the most recent eleven outputs from said converter and said averaging means averages the seven oldest values in said storage means.

4. In an optical system where light from a source is transmitted through a sample to measure the absorbance of light by the sample, the improvement of an automatic blanking circuit to continually compensate for variations and degradation in the intensity of light received by a photodetector which photodetector provides an output signal proportional to the intensity of the light it receives, said improvement comprising:

means to amplify the output of said photodetector;
a source of reference voltage;
dual input comparator means, said first input being from said amplifier means and said second input being from said source of reference voltage, said dual input comparator means providing an output when said reference voltage exceeds the output of said amplifier means;

counter means to measure the time interval during which said comparator means provides an output;

storage means to serially store a plurality of sequential outputs of said counter means; and arithmetic means to average selected values from said storage means.

5. The invention as defined in claim 4 wherein said amplifier means includes an adjustable voltage divider to attenuate the amplifier output so that the output of said amplifier means in the absence of any sample equals the output of said amplifier means when the sample is water.

6. The invention as defined in claim 4 wherein said arithmetic means and said storage means cooperate so that upon averaging of said selected values in storage, said plurality of sequential outputs stored in said serial storage means are replaced by said average value.

7. The invention as defined in claim 4 wherein said source of reference voltage is an exponentially decaying voltage.

8. The invention as defined in claim 4, wherein said source of reference voltage includes a capacitor and a resistor with said capacitor being charged to a first voltage and discharging through said resistor, said voltage on said capacitor being provided as said second input to said dual input comparator means.

9. In an optical system where light from a source is transmitted through a sample to measure the absorbance of light by the sample, the improvement of a method for continually compensating for variations in the intensity of the light received by a photodetector, such as those caused by age, deterioration, dirt or the like, comprising the steps of:

providing a source of reference voltage;

comparing the reference voltage to the output of said photodetector;

providing a digital value representative of the time during which the reference voltage exceeds the intensity of light received by said photodetector;

serially storing a first predetermined number of said digital value; and averaging a second predetermined number of the serially stored values and providing an output; said second predetermined number being less than said first predetermined number.

10. The invention as defined in claim 9 wherein said first predetermined number is eleven and said second predetermined number is seven.

11. In an optical system where light from a source is transmitted through a sample to measure the absorbance of light by the sample, the improvement of an automatic blanking method to continually compensate for variations and degradation in the intensity of light received by a photodetector which photodetector provides an output signal proportional to the intensity of the light it receives, said improvement comprising the steps of:

amplifying the output of said photodetector;

providing a source of reference voltage;

comparing the output from said amplifier means with said source of reference voltage and providing an output when said reference voltage exceeds the output of said amplifier;

counting the duration of the time during which said step of comparing provides an output;

serially storing a plurality of sequential outputs from said step of counting; and averaging selected values which are serially stored.

12. The invention as defined in claim 11 wherein said step of averaging includes replacing the serially stored outputs with the result of said averaging.

* * * * *